(12) United States Patent
Indusegaram et al.

(10) Patent No.: US 7,825,262 B2
(45) Date of Patent: Nov. 2, 2010

(54) ONE-POT PREPARATION OF A BENZOISOINDOLENINE SALT FROM A TETRAHYDRONAPHTHALIC ANHYDRIDE

(75) Inventors: Sutharsiny Indusegaram, Balmain (AU); Simone Charlotte Vonwiller, Balmain (AU); Damon Donald Ridley, Balmain (AU); Kia Silverbrook, Balmain (AU)

(73) Assignee: Silverbrook Research Pty Ltd, Balmain, New South Wales (AU)

( * ) Notice: Subject to any disclaimer, the term of this patent is extended or adjusted under 35 U.S.C. 154(b) by 626 days.

(21) Appl. No.: 11/831,962

(22) Filed: Aug. 1, 2007

(65) Prior Publication Data

US 2009/0036671 A1 Feb. 5, 2009

(51) Int. Cl.
*C07D 209/58* (2006.01)
(52) U.S. Cl. ..................................... 548/427
(58) Field of Classification Search .................. 548/427
See application file for complete search history.

(56) References Cited

U.S. PATENT DOCUMENTS 7,365,061 B2 4/2008 Sher et al.

FOREIGN PATENT DOCUMENTS

GB 1306055 A 2/1973

JP 10-059974 A 3/1998

OTHER PUBLICATIONS

Suzuki, S et al (1977) "Synthesis of Finely Powdered Copper Phthalocynanine in Decalin" Nippon Kagaky Kaishi 8:1250-1252 [See Whole Document].
Uchida H et al (2003) "Novel Synthesis of Metal Free Phthalocynanines from Phthalimides and Phthalic Anhydrides with Hexamethyldisilazane" Synlett 13:2083-2085 [See Scheme 1, p. 2083, where X=O; Table 1; Scheme 2].
Uchida H et al (2003) "Novel Efficient Preparative Method for Phthalocynanines from Phthalimides and Phthalic Anhydrides with HMDS" Journal of Organic Chemistry 68:8736-8738 [See p. 8737, col. 1, last paragraph].
Brumfield SN et al (1962) "Formation of Copper Phthalocynanine" Journal of Organic Chemistry 27:2266-2267 [See whole document].

*Primary Examiner*—James O Wilson
*Assistant Examiner*—Brian McDowell

(57) ABSTRACT

A method of effecting a one-pot conversion of a tetrahydronaphthalic anhydride to a benzisoindolenine salt is provided. The method comprises heating the tetrahydronaphthalic anhydride with a reagent mixture comprising ammonium nitrate.

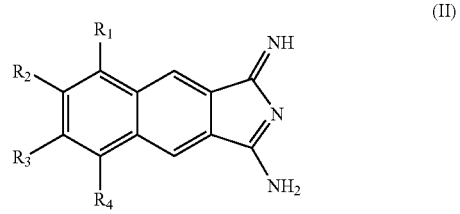

11 Claims, 7 Drawing Sheets

ONE-POT PREPARATION OF A BENZOISOINDOLENINE SALT FROM A TETRAHYDRONAPHTHALIC ANHYDRIDE

FIELD OF THE INVENTION

The present application relates generally to an improved method of synthesizing naphthalocyanines. It has been developed primarily to reduce the cost of existing naphthalocyanine syntheses and to facilitate large-scale preparations of these compounds.

CROSS REFERENCE TO OTHER RELATED APPLICATIONS

The following applications have been filed by the Applicant simultaneously with this application:
IRB023US IRB025US
The disclosure of these co-pending applications are incorporated herein by reference. The above applications have been identified by their filing docket number, which will be substituted with the corresponding application number, once assigned.

The following patents or patent applications filed by the applicant or assignee of the present invention are hereby incorporated by cross-reference.

10/815,621 10/815,612 10/815,630 10/815,637 10/815,638 10/815,640 10/815,642 7,097,094 7,137,549 10/815,618 7,156,292 11,738,974 10/815,635 10/815,647 10/815,634 7,137,566 7,131,596 7,128,265 7,207,485 7,197,374 7,175,089 10/815,617 10/815,620 7,178,719 10/815,613 7,207,483 10/815,619 10/815,616 10/815,614 11/488,162 11/488,163 11/488,164 11/488,167 11/488,168 11/488,165 11/488,166 11/499,748 10/815,636 7,128,270 11/41,650 11/41,651 11/41,652 11/41,649 11/41,610 11/41,609 11/41,626 11/41,627 11/41,624 11/41,625 11/41,556 11/41,580 11/41,723 11/41,698 11/41,648 10/815,609 7,150,398 7,159,777 10/815,610 7,188,769 7,097,106 7,070,110 7,243,849 11/480,957 11,764,694 7,204,941 10/815,624 10/815,628 10/913,375 10/913,373 10/913,374 10/913,372 7,138,391 7,153,956 10/913,380 10/913,379 10/913,376 7,122,076 7,148,345 11/172,816 11/172,815 11/172,814 11/482,990 11/482,986 11/482,985 11/583,942 11/592,990 60/851,754 11/756,624 11/566,625 11/756,626 11/756,627 11/756,629 11/756,630 11/756,631 7,156,289 7,178,718 7,225,979 11/712,434 11/84,796 11/84,742 11/84,806 9/575,197 7,079,712 9/575,123 6,825,945 9/575,165 6,813,039 7,190,474 6,987,506 6,824,044 7,038,797 6,980,318 6,816,274 7,102,772 9/575,186 6,681,045 6,678,499 6,679,420 6,963,845 6,976,220 6,728,000 7,110,126 7,173,722 6,976,035 6,813,558 6,766,942 6,965,454 6,995,859 7,088,459 6,720,985 9/609,303 6,922,779 6,978,019 6,847,883 7,131,058 9/721,895 9/607,843 9/693,690 6,959,298 6,973,450 7,150,404 6,965,882 7,233,924 9/575,181 9/722,174 7,175,079 7,162,259 6,718,061 10/291,523 10/291,471 7,012,710 6,825,956 10/291,481 7,222,098 10/291,825 10/291,519 7,031,010 6,972,864 6,862,105 7,009,738 6,989,911 6,982,807 10/291,576 6,829,387 6,714,678 6,644,545 6,609,653 6,651,879 10/291,555 10/291,510 10/291,592 10/291,542 7,044,363 7,004,390 6,867,880 7,034,953 6,987,581 7,216,224 10/291,821 7,162,269 7,162,222 10/291,822 10/291,524 10/291,553 6,850,931 6,865,570 6,847,961 10/685,523 10/685,583 7,162,442 10/685,584 7,159,784 10/804,034 10/793,933 6,889,896 10/831,232 7,174,056 6,996,274 7,162,088 10/943,874 10/943,872 10/944,044 10/943,942 10/944,043 7,167,270 10/943,877 6,986,459 10/954,170 7,181,448 10/981,626 10/981,616 10/981,627 7,231,293 7,174,329 10/992,713 11/6,536 7,200,591 11/20,106 11/20,260 11/20,321 11/20,319 11/26,045 11/59,696 11/51,032 11/59,674 11/107,944 11/107,941 11/82,940 11/82,815 11/82,827 11/82,829 6,991,153 6,991,154 11/124,256 11/123,136 11/154,676 11/159,196 11/182,002 11/202,251 11/202,252 11/202,253 11/203,200 11/202,218 11/206,778 11/203,424 11/222,977 11/228,450 11/227,239 11/286,334 7,225,402 11/349,143 11/442,428 11/442,385 11/478,590 11/487,499 11/520,170 11/603,057 11/706,964 11/739,032 11,739,014 7,068,382 7,007,851 6,957,921 6,457,883 10/743,671 7,044,381 11/203,205 7,094,910 7,091,344 7,122,685 7,038,066 7,099,019 7,062,651 6,789,194 6,789,191 10/900,129 10/900,127 10/913,350 10/982,975 10/983,029 11/331,109 6,644,642 6,502,614 6,622,999 6,669,385 6,827,116 7,011,128 10/949,307 6,549,935 6,987,573 6,727,996 6,591,884 6,439,706 6,760,119 9/575,198 7,064,851 6,826,547 6,290,349 6,428,155 6,785,016 6,831,682 6,741,871 6,927,871 6,980,306 6,965,439 6,840,606 7,036,918 6,977,746 6,970,264 7,068,389 7,093,991 7,190,491 10/901,154 10/932,044 10/962,412 7,177,054 10/962,552 10/965,733 10/965,933 10/974,742 10/982,974 7,180,609 10/986,375 11/107,817 11/148,238 11/149,160 11/250,465 7,202,959 11/653,219 11/706,309 11/730,392 6,982,798 6,870,966 6,822,639 6,474,888 6,627,870 6,724,374 6,788,982 9/722,141 6,788,293 6,946,672 6,737,591 7,091,960 9/693,514 6,792,165 7,105,753 6,795,593 6,980,704 6,768,821 7,132,612 7,041,916 6,797,895 7,015,901 10/782,894 7,148,644 10/778,056 10/778,058 10/778,060 10/778,059 10/778,063 10/778,062 10/778,061 10/778,057 7,096,199 10/917,468 10/917,467 10/917,466 10/917,465 7,218,978 7,245,294 10/948,253 7,187,370 10/917,436 10/943,856 10/919,379 7,019,319 10/943,878 10/943,849 7,043,096 7,148,499 11/144,840 11/155,556 11/155,557 11/193,481 11/193,435 11/193,482 11/193,479 11/255,941 11/281,671 11/298,474 7,245,760 11/488,832 11/495,814 11/495,823 11/495,822 11/495,821 11/495,820 11/653,242 11/754,370 60,911,260 7,055,739 7,233,320 6,830,196 6,832,717 7,182,247 7,120,853 7,082,562 6,843,420 10/291,718 6,789,731 7,057,608 6,766,944 6,766,945 10/291,715 10/291,559 10/291,660 10/531,734 10/409,864 7,108,192 10/537,159 7,111,791 7,077,333 6,983,878 10/786,631 7,134,598 10/893,372 6,929,186 6,994,264 7,017,826 7,014,123 7,134,601 7,150,396 10/971,146 7,017,823 7,025,276 10/990,459 7,080,780 11/74,802 11/442,366 11/749,158 10/492,169 10/492,152 10/492,168 10/492,161 10/492,154 10/502,575 10/531,229 10/683,151 10/531,733 10/683,040 10/510,391 10/510,392 10/778,090 6,957,768 9/575,172 7,170,499 7,106,888 7,123,239 6,982,701 6,982,703 7,227,527 6,786,397 6,947,027 6,975,299 7,139,431 7,048,178 7,118,025 6,839,053 7,015,900

-continued

| | | | | | |
|---|---|---|---|---|---|
| 7,010,147 | 7,133,557 | 6,914,593 | 10/291,546 | 6,938,826 | 10/913,340 |
| | | | | | 7,123,245 |
| 6,992,662 | 7,190,346 | 11/74,800 | 11/74,782 | 11/74,777 | 11/75,917 |
| | | | | | 7,221,781 |
| 11/102,843 | 7,213,756 | 11/188,016 | 7,180,507 | 11/202,112 | 11/442,114 |
| | | | | | 11/737,094 |
| 11/753,570 | 60/829,869 | 60/829,871 | 60/829,873 | 11/672,522 | 11/672,950 |
| | | | | | 11/672,947 |
| 11/672,891 | 11/672,954 | 11/672,533 | 11/754,310 | 11/754,321 | 11/754,320 |
| | | | | | 11/754,319 |
| 11/754,318 | 11/754,317 | 11/754,316 | 11/754,315 | 11/754,314 | 11/754,313 |
| | | | | | 11/754,312 |
| 11/754,311 | 11/743,657 | 6,454,482 | 6,808,330 | 6,527,365 | 6,474,773 |
| | | | | | 6,550,997 |
| 7,093,923 | 6,957,923 | 7,131,724 | 10/949,288 | 7,168,867 | 7,125,098 |
| | | | | | 11/706,966 |
| 11/185,722 | 11/181,754 | 7,188,930 | | | |

BACKGROUND OF THE INVENTION

We have described previously the use of naphthalocyanines as IR-absorbing dyes. Naphthalocyanines, and particularly gallium naphthalocyanines, have low absorption in the visible range and intense absorption in the near-IR region (750-810 nm). Accordingly, naphthalocyanines are attractive compounds for use in invisible inks. The Applicant's U.S. Pat. Nos. 7,148,345 and 7,122,076 (the contents of which are herein incorporated by reference) describe in detail the use of naphthalocyanine dyes in the formulation of inks suitable for printing invisible (or barely visible) coded data onto a substrate. Detection of the coded data by an optical sensing device can be used to invoke a response in a remote computer system. Hence, the substrate is interactive by virtue of the coded data printed thereon.

The Applicant's netpage and Hyperlabel® systems, which makes use of interactive substrates printed with coded data, are described extensively in the cross-referenced patents and patent applications above (the contents of which are herein incorporated by reference).

In the anticipation of widespread adoption of netpage and Hyperlabel® technologies, there exists a considerable need to develop efficient syntheses of dyes suitable for use in inks for printing coded data. As foreshadowed above, naphthalocyanines and especially gallium naphthalocyanines are excellent candidates for such dyes and, as a consequence, there is a growing need to synthesize naphthalocyanines efficiently and in high yield on a large scale.

Naphthalocyanines are challenging compounds to synthesize on a large-scale. In U.S. Pat. Nos. 7,148,345 and 7,122,076, we described an efficient route to naphthalocyanines via macrocyclization of naphthalene-2,3-dicarbonitrile. Scheme 1 shows a route to the sulfonated gallium naphthalocyanine 1 from naphthalene-2,3-dicarbonitrile 2, as described in U.S. Pat. No. 7,148,345.

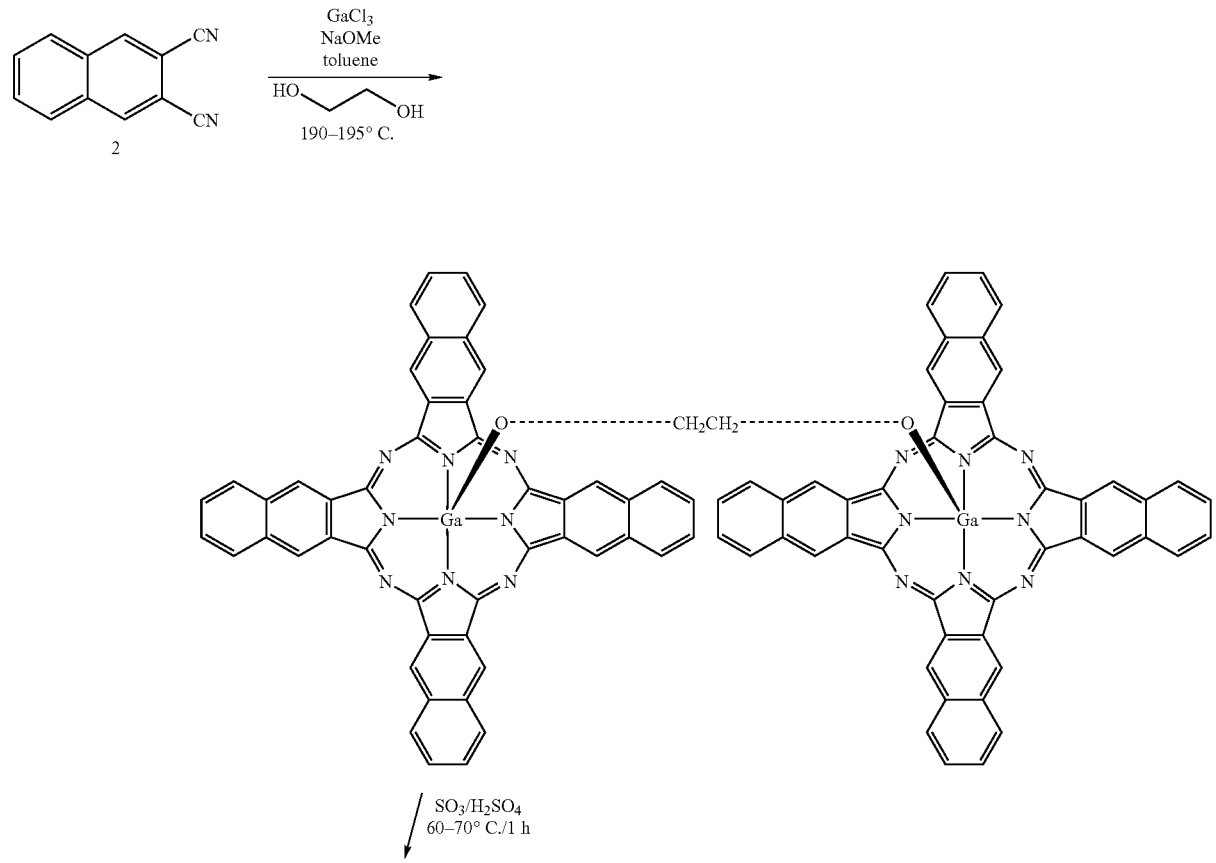

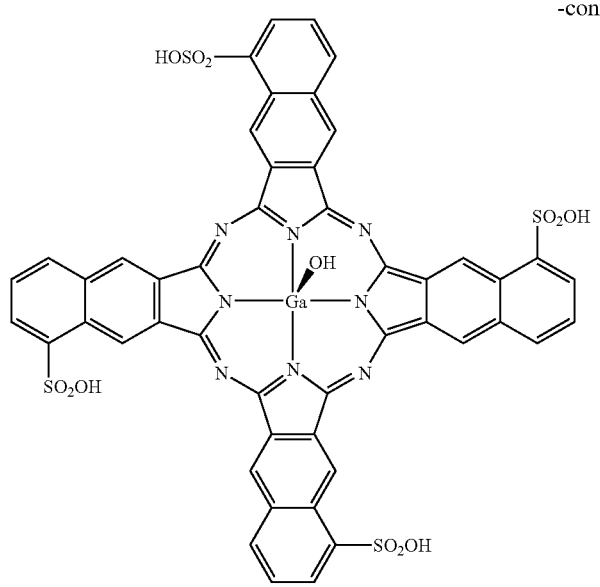

1

However, a problem with this route to naphthalocyanines is that the starting material 2 is expensive. Furthermore, naphthalene-2,3-dicarbonitrile 2 is prepared from two expensive building blocks: tetrabromo-o-xylene 3 and fumaronitrile 4, neither of which can be readily prepared in multi-kilogram quantities.

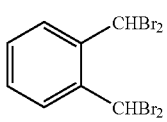

3

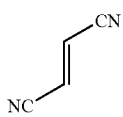

4

Accordingly, if naphthalocyanines are to be used in large-scale applications, there is a need to improve on existing syntheses.

SUMMARY OF THE INVENTION

In a first aspect, there is provided a method of preparing a naphthalocyanine comprising the steps of:
(i) providing a tetrahydronaphthalic anhydride;
(ii) converting said tetrahydronaphthalic anhydride to a benzisoindolenine; and
(iii) macrocyclizing said benzisoindolenine to form a naphthalocyanine.

Optionally, the tetrahydronaphthalic anhydride is of formula (I):

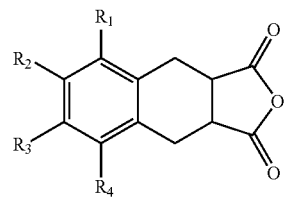

wherein:
$R_1$, $R_2$, $R_3$ and $R_4$ are each independently selected from hydrogen, hydroxyl, $C_{1-20}$alkyl, $C_{1-20}$alkoxy, amino, $C_{1-20}$alkylamino, di($C_{1-20}$alkyl)amino, halogen, cyano, thiol, $C_{1-20}$alkylthio, nitro, $C_{1-20}$alkylcarboxy, $C_{1-20}$alkylcarbonyl, $C_{1-20}$alkoxycarbonyl, $C_{1-20}$alkylcarbonyloxy, $C_{1-20}$alkylcarbonylamino, $C_{5-20}$aryl, $C_{5-20}$arylalkyl, $C_{5-20}$aryloxy, $C_{5-20}$arylalkoxy, $C_{5-20}$heteroaryl, $C_{5-20}$heteroaryloxy, $C_{5-20}$heteroarylalkoxy or $C_{5-20}$heteroarylalkyl.

Optionally, $R_1$, $R_2$, $R_3$ and $R_4$ are all hydrogen.

Optionally, step (ii) comprises a one-pot conversion from the tetrahydronaphthalic anhydride to a benzisoindolenine salt. This one-pot conversion facilitates synthesis of naphthalocyanines via the route described above and greatly improves yields and scalability.

Optionally, the benzisoindolenine salt is a nitrate salt although other salts (e.g. benzene sulfonate salt) are of course within the scope of the present invention.

Optionally, the one-pot conversion is effected by heating with a reagent mixture comprising ammonium nitrate.

Optionally, the reagent mixture comprises at least 2 equivalents of ammonium nitrate with respect to the tetrahydronaphthalic anhydride.

Optionally, the reagent mixture comprises urea.

Optionally, the reagent mixture comprises at least one further ammonium salt.

Optionally, the further ammonium salt is selected from: ammonium sulfate and ammonium benzenesulfonate Optionally, the reagent mixture comprises a catalytic amount of ammonium molybdate.

Optionally, the heating is within a temperature range of 150 to 200° C.

The reaction may be performed in the presence of or in the absence of a solvent. Optionally, heating is in the presence of an aromatic solvent. Examples of suitable solvents are nitrobenzene, biphenyl, diphenyl ether, mesitylene, anisole, phenetole, dichlorobenzene, trichlorobenzene and mixtures thereof.

Optionally, the benzisoindolenine is liberated from the benzisoindolenine salt using a base. Sodium methoxide is an example of a suitable base although the skilled person will be readily aware of other suitable bases.

Optionally, the benzisoindolenine is of formula (II):

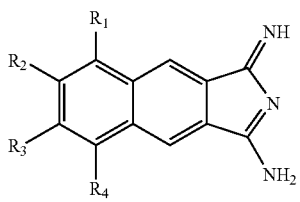

(II)

wherein:

$R_1$, $R_2$, $R_3$ and $R_4$ are each independently selected from hydrogen, hydroxyl, $C_{1-20}$alkyl, $C_{1-20}$alkoxy, amino, $C_{1-20}$alkylamino, di($C_{1-20}$alkyl)amino, halogen, cyano, thiol, $C_{1-20}$alkylthio, nitro, $C_{1-20}$alkylcarboxy, $C_{1-20}$alkylcarbonyl, $C_{1-20}$alkoxycarbonyl, $C_{1-20}$alkylcarbonyloxy, $C_{1-20}$alkylcarbonylamino, $C_{5-20}$aryl, $C_{5-20}$arylalkyl, $C_{5-20}$aryloxy, $C_{5-20}$arylalkoxy, $C_{5-20}$heteroaryl, $C_{5-20}$heteroaryloxy, $C_{5-20}$heteroarylalkoxy or $C_{5-20}$heteroarylalkyl.

Optionally, the naphthalocyanine is of formula (III):

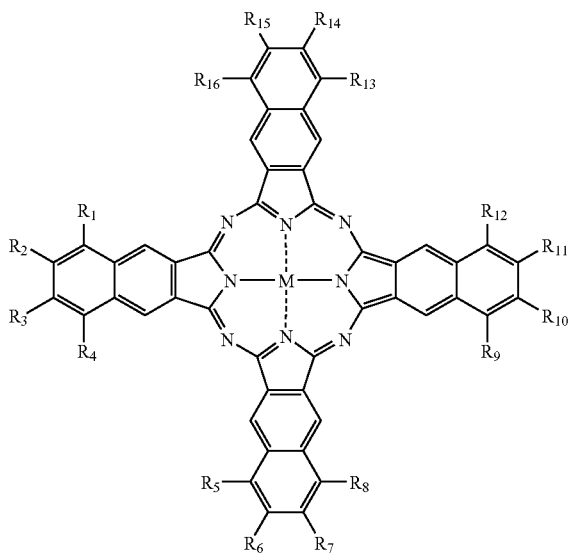

(III)

wherein:

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are each independently selected from hydrogen, hydroxyl, $C_{1-20}$alkyl, $C_{1-20}$alkoxy, amino, $C_{1-20}$alkylamino, di($C_{1-20}$alkyl)amino, halogen, cyano, thiol, $C_{1-20}$alkylthio, nitro, $C_{1-20}$alkylcarboxy, $C_{1-20}$alkylcarbonyl, $C_{1-20}$alkoxycarbonyl, $C_{1-20}$alkylcarbonyloxy, $C_{1-20}$alkylcarbonylamino, $C_{5-20}$aryl, $C_{5-20}$arylalkyl, $C_{5-20}$aryloxy, $C_{5-20}$arylalkoxy, $C_{5-20}$heteroaryl, $C_{5-20}$heteroaryloxy, $C_{5-20}$heteroarylalkoxy or $C_{5-20}$heteroarylalkyl;

M is absent or selected from $Si(A^1)(A^2)$, $Ge(A^1)(A^2)$, $Ga(A^1)$, Mg, $Al(A^1)$, TiO, $Ti(A^1)(A^2)$, ZrO, $Zr(A^1)(A^2)$, VO, $V(A^1)(A^2)$, Mn, $Mn(A^1)$, Fe, $Fe(A^1)$, Co, Ni, Cu, Zn, Sn, $Sn(A^1)(A^2)$, Pb, $Pb(A^1)(A^2)$, Pd and Pt;

$A^1$ and $A^2$ are axial ligands, which may be the same or different, and are selected from —OH, halogen, or —$OR^q$;

$R^q$ is selected from $C_{1-16}$alkyl, $C_{5-20}$aryl, $C_{5-20}$arylalkyl, $C_{1-20}$alkylcarbonyl, $C_{1-20}$alkoxycarbonyl or $Si(R^x)(R^y)(R^z)$; and $R^x$, $R^y$ and $R^z$ may be the same or different and are selected from $C_{1-20}$alkyl, $C_{5-20}$aryl, $C_{5-20}$arylalkyl, $C_{1-20}$alkoxy, $C_{5-20}$aryloxy or $C_{5-20}$arylalkoxy;

Optionally, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are all hydrogen.

Optionally, M is $Ga(A^1)$, such as $Ga(OCH_2CH_2OCH_2CH_2OCH_2CH_2OMe)$; that is where $R^q$ is $CH_2CH_2OCH_2CH_2OCH_2CH_2OMe$. For the avoidance of doubt, ethers such as $CH_2CH_2OCH_2CH_2OCH_2CH_2OMe$ fall within the definition of alkyl groups as specified hereinbelow. Gallium compounds are preferred since they have excellent lightfastness, strong absorption in the near-IR region, and are virtually invisible to the human eye when printed on a page.

Optionally, step (iii) comprises heating the benzisoindolenine in the presence of a metal compound, such as $AlCl_3$ or $GaCl_3$ or a corresponding metal alkoxide. The reaction may be performed in the absence of or in the presence of a suitable solvent, such as toluene, nitrobenzene etc. When a metal alkoxide is used, the reaction may be catalyzed with a suitable base, such as sodium methoxide. Alcohols, such as triethylene glycol monomethyl ether or glycol may also be present to assist with naphthalocyanine formation. These alcohols may end up as the axial ligand of the naphthalocyanine or they may be cleaved from the metal under the reaction conditions. The skilled person will readily be able to optimize the conditions for naphthalocyanine formation from the benzisoindolenine.

Optionally, the method further comprises the step of sulfonating said naphthalocyanine. Sulfonate groups are useful for solubilizing the naphthalocyanines in ink formulations, as described in our earlier U.S. Pat. Nos. 7,148,345 and 7,122,076.

In a second aspect, there is provided a method of effecting a one-pot conversion of a tetrahydronaphthalic anhydride to a benzisoindolenine salt, said method comprising heating said tetrahydronaphthalic anhydride with a reagent mixture comprising ammonium nitrate.

This transformation advantageously obviates a separate dehydrogenation step to form the naphthalene ring system. The ammonium nitrate performs the dual functions of oxidation (dehydrogenation) and isoindolenine formation.

The isoindolenine salts generated according to the second aspect may be used in the synthesis of naphthalocyanines. Hence, this key reaction provides a significant improvement in routes to naphthalocyanines.

In general, optional features of this second aspect mirror the optional features described above in respect of the first aspect.

In a third aspect, there is provided a method of preparing a sultine of formula (V) from a dihalogeno compound of formula (IV)

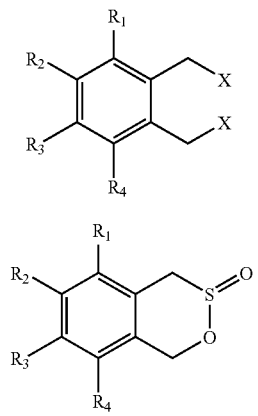

the method comprising reacting the dihalogeno compound (IV) with a hydroxymethanesulfinate salt in a DMSO solvent so as to prepare the sultine (V);

wherein:

$R_1$, $R_2$, $R_3$ and $R_4$ are each independently selected from hydrogen, hydroxyl, $C_{1-20}$alkyl, $C_{1-20}$alkoxy, amino, $C_{1-20}$alkylamino, di($C_{1-20}$alkyl)amino, halogen, cyano, thiol, $C_{1-20}$alkylthio, nitro, $C_{1-20}$alkylcarboxy, $C_{1-20}$alkylcarbonyl, $C_{1-20}$alkoxycarbonyl, $C_{1-20}$alkylcarbonyloxy, $C_{1-20}$alkylcarbonylamino, $C_{5-20}$aryl, $C_{5-20}$arylalkyl, $C_{5-20}$aryloxy, $C_{5-20}$arylalkoxy, $C_{5-20}$heteroaryl, $C_{5-20}$heteroaryloxy, $C_{5-20}$heteroarylalkoxy or $C_{5-20}$heteroarylalkyl; and X is Cl, Br or I.

The method according to the third aspect surprisingly minimizes polymeric by-products and improves yields, when compared to literature methods for this reaction employing DMF as the solvent. These advantages are amplified when the reaction is performed on a large scale (e.g. at least 0.3 molar, at least 0.4 molar or at least 0.5 molar scale).

Optionally, NaI is used to catalyze the coupling reactions when X is Cl or Br.

Optionally, a metal carbonate base (e.g. $Na_2CO_3$, $K_2CO_3$, $Cs_2CO_3$ etc) is present.

Optionally, the hydroxymethanesulfinate salt is sodium hydroxymethanesulfinate (Rongalite™).

Optionally, $R_1$, $R_2$, $R_3$ and $R_4$ are all hydrogen.

Optionally, the method comprises the further step of reacting the sultine (V) with an olefin at elevated temperature (e.g. about 80° C.) to generate a Diels-Alder adduct.

Optionally, the olefin is maleic anhydride and said Diels-Alder adduct is a tetrahydronaphthalic anhydride.

Optionally, the tetrahydronaphthalic anhydride is used as a precursor for naphthalocyanine synthesis, as described herein.

Optionally, the naphthalocyanine synthesis proceeds via conversion of the tetrahydronaphthalic anhydride to a benzisoindolenine, as described herein.

BRIEF DESCRIPTION OF THE DRAWINGS

The invention will now be described in detail with reference to the following drawings, in which.

DETAILED DESCRIPTION

Figure 1:
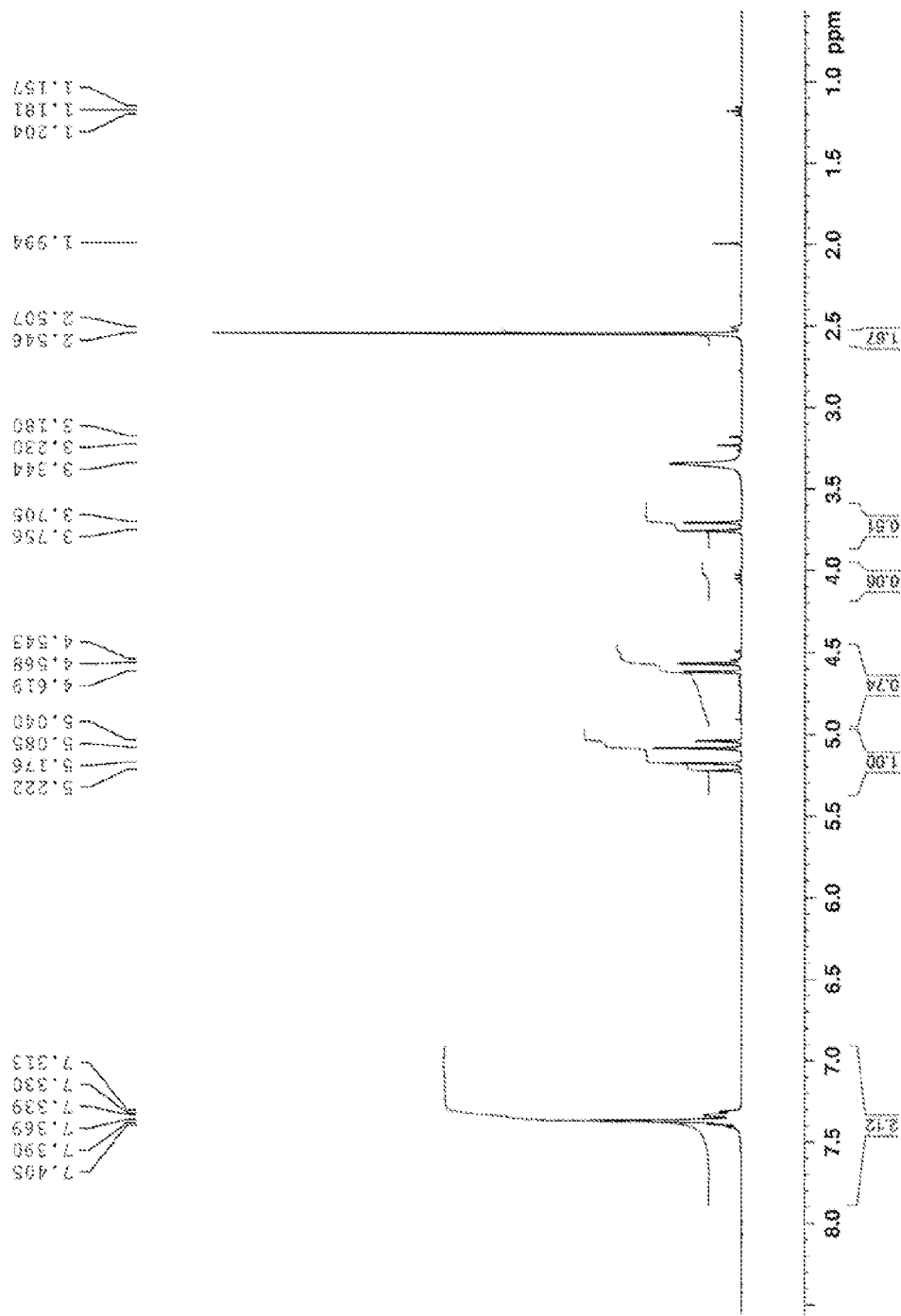
FIG. 1 is a $^1$H NMR spectrum of the crude sultine 10 in $d_6$-DMSO.
Figure 2:
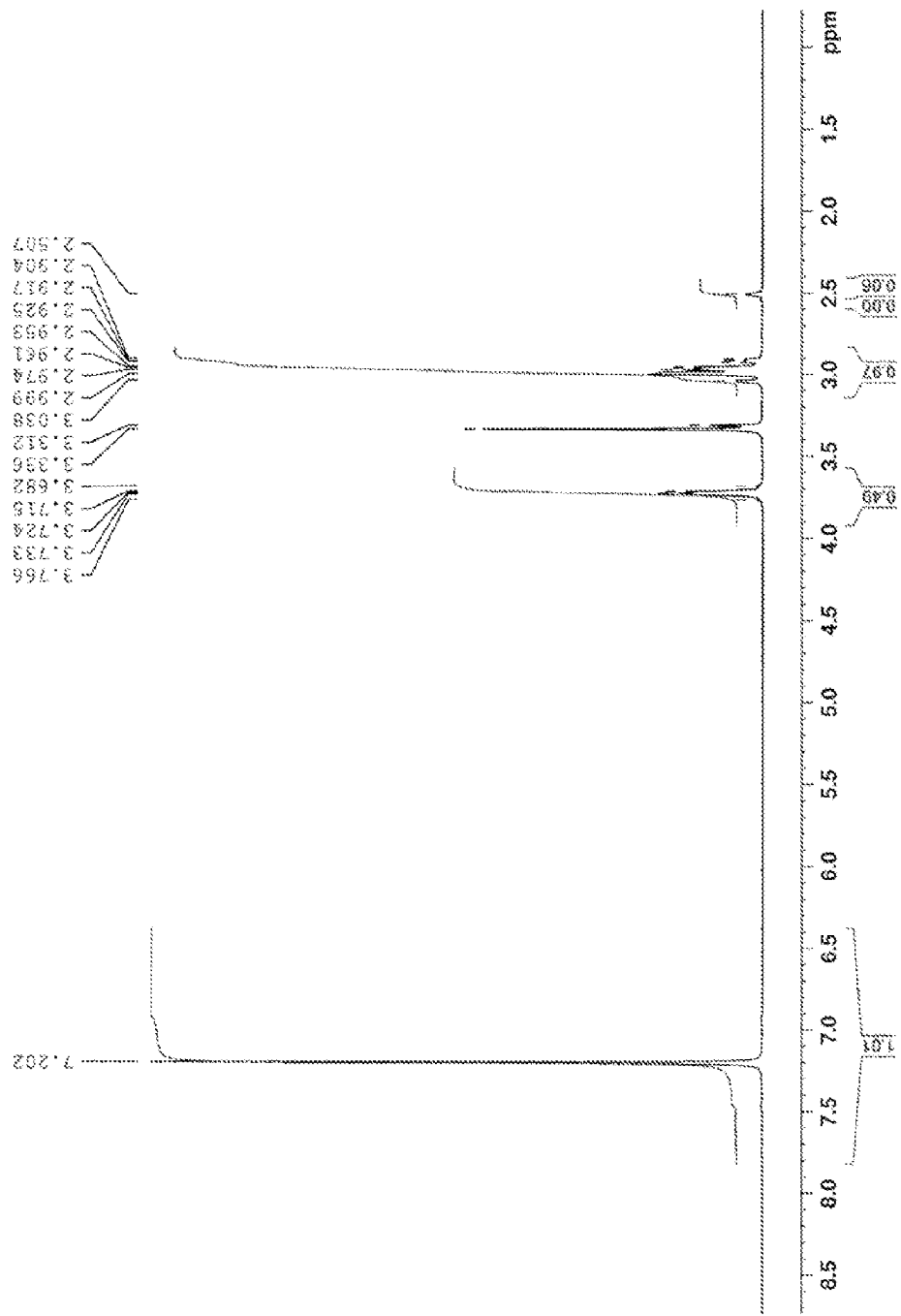
FIG. 2 is a $^1$H NMR spectrum of the anhydride 8 in $d_6$-DMSO.
Figure 3:
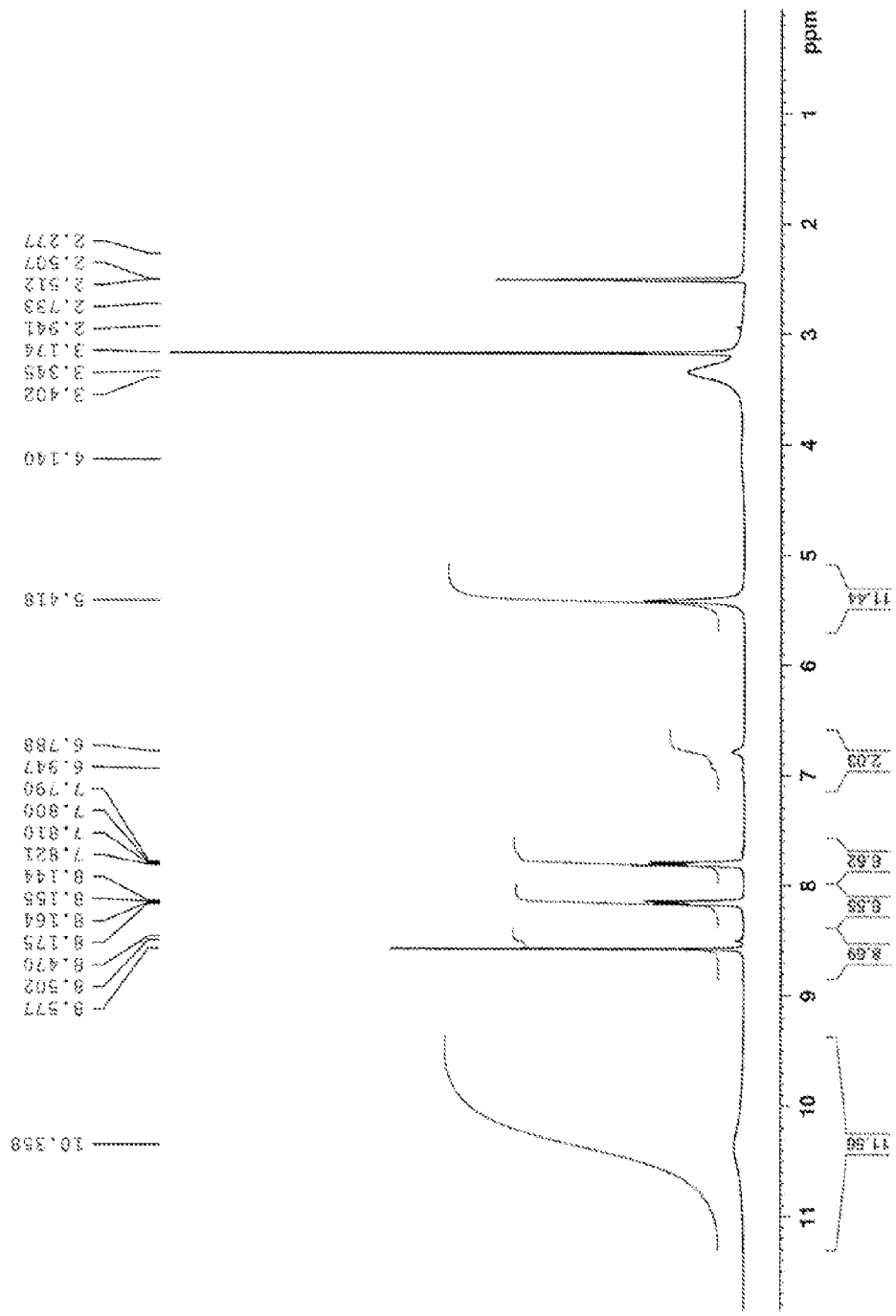
FIG. 3 is a $^1$H NMR spectrum of the crude benzisoindolenine salt 12 in $d_6$-DMSO.
Figure 4:
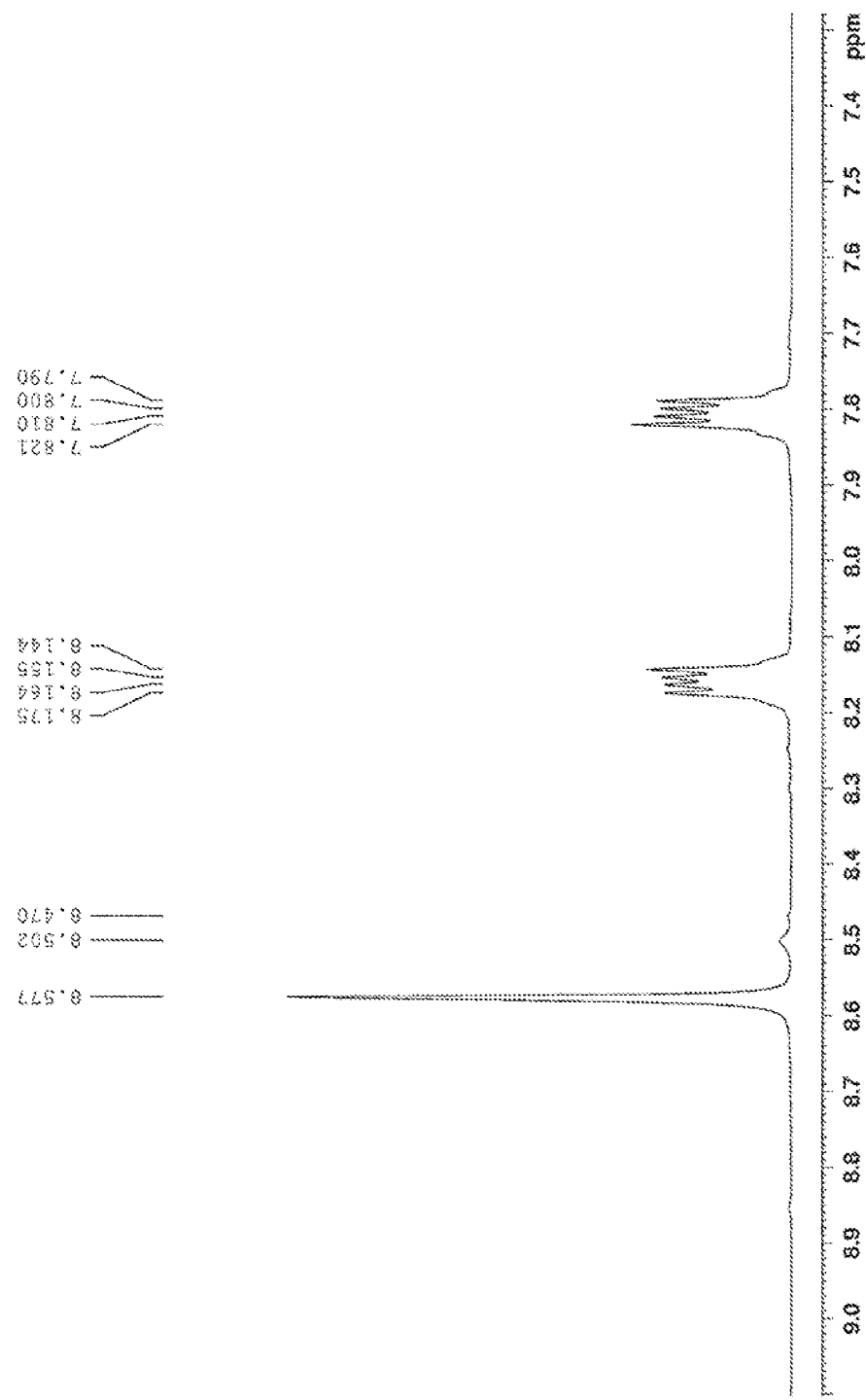
FIG. 4 is an expansion of the aromatic region of the $^1$H NMR spectrum shown in FIG. 3.
Figure 5:
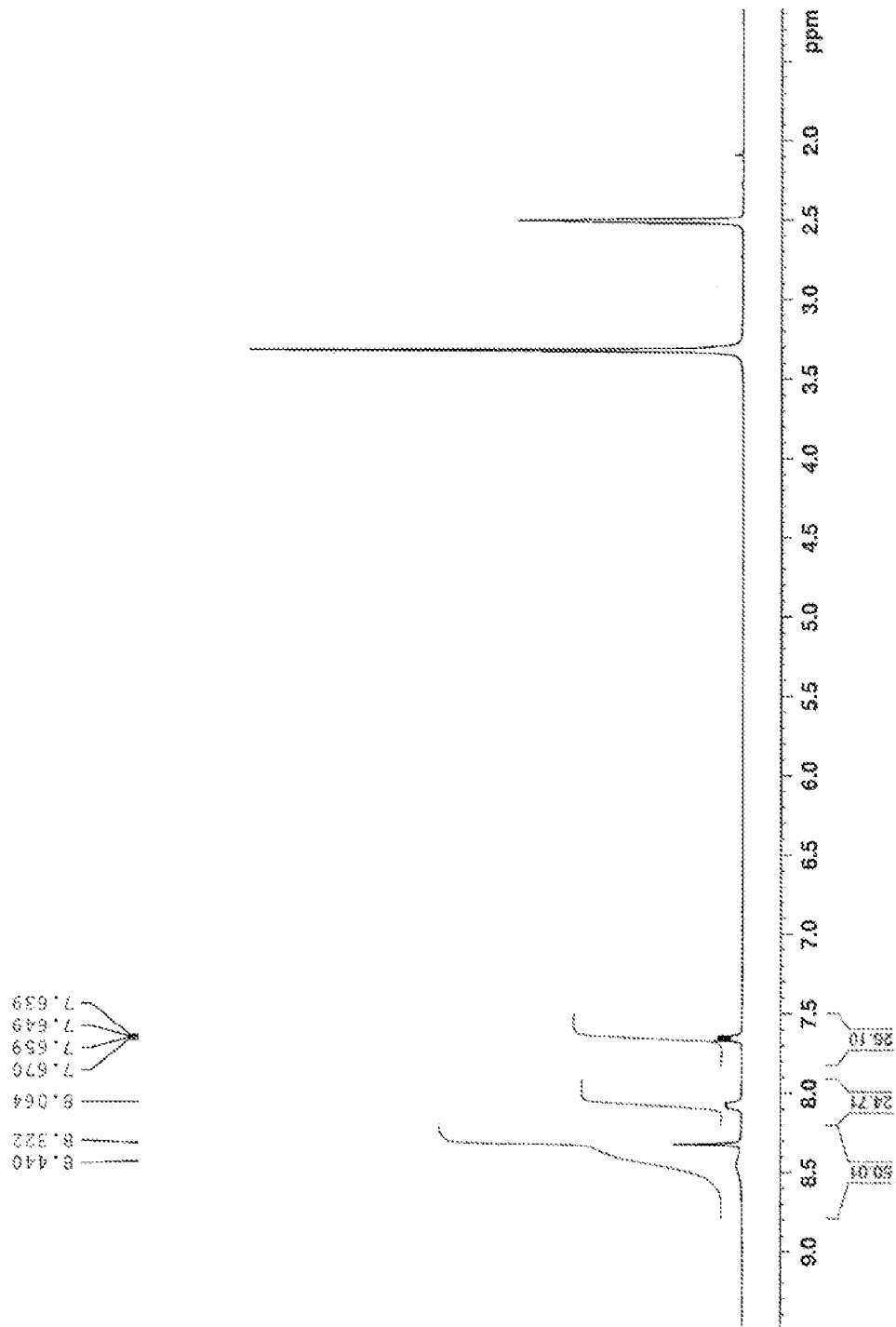
FIG. 5 is a $^1$H NMR spectrum of the benzisoindolenine 7 in $d_6$-DMSO.
Figure 6:
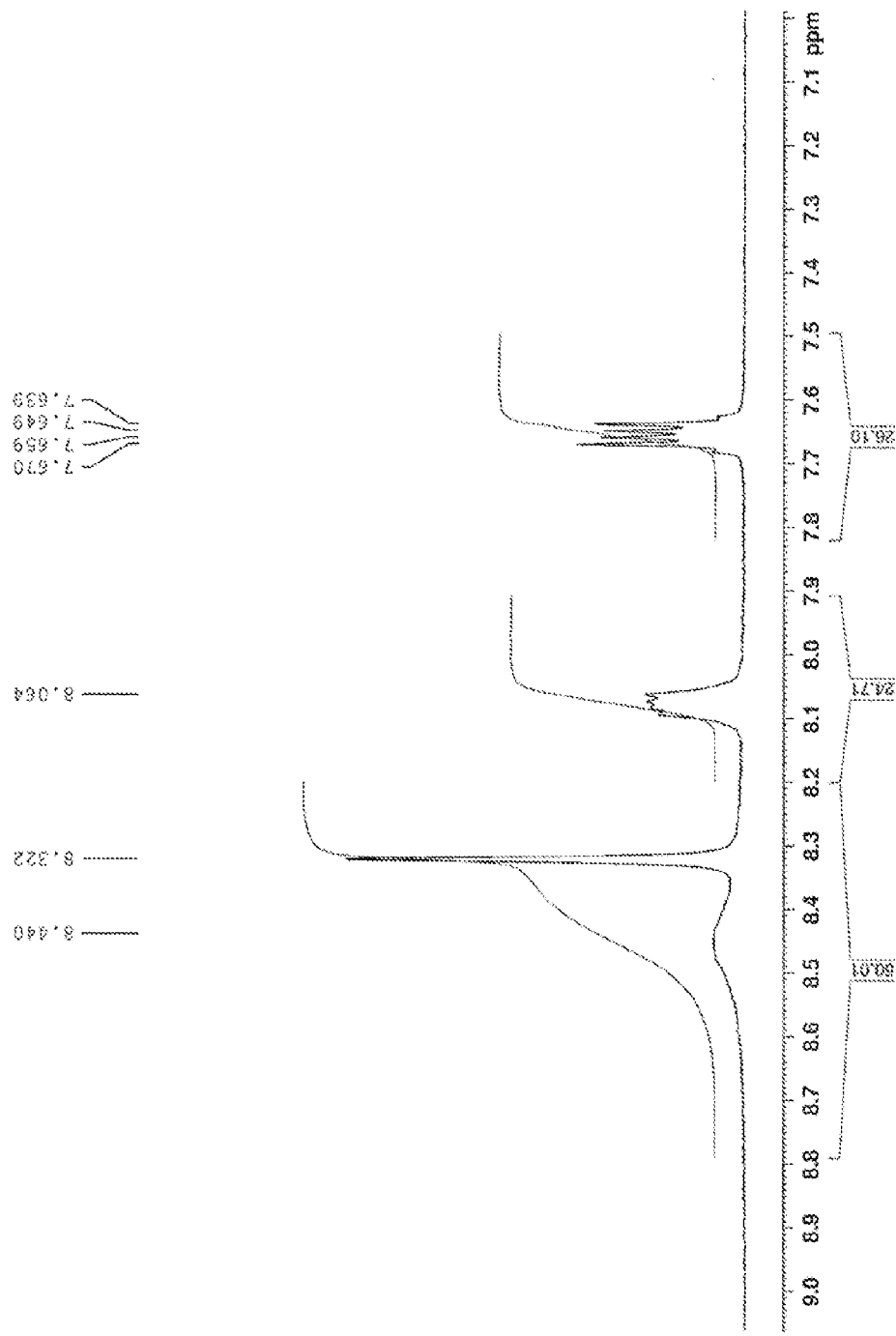
FIG. 6 is an expansion of the aromatic region of the $^1$H NMR spectrum shown in FIG. 5.

As an alternative to dicarbonitriles, the general class of phthalocyanines is known to be prepared from isoindolenines. In U.S. Pat. No. 7,148,345, we proposed the benzisoindolenine 5 as a possible precursor to naphthalocyanines.

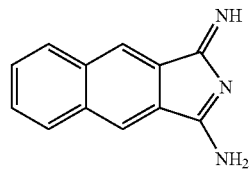

However, efficient syntheses of the benzisoindolenine 5 were unknown in the literature, and it was hitherto understood that dicarbonitriles, such as naphthalene-2,3-dicarbonitrile 2, were the only viable route to naphthalocyanines.

Nevertheless, with the potentially prohibitive cost of naphthalene-2,3-dicarbonitrile 2, the present inventors sought to explore a new route to the benzisoindolenine 5, as outlined in Scheme 2.

Scheme 2

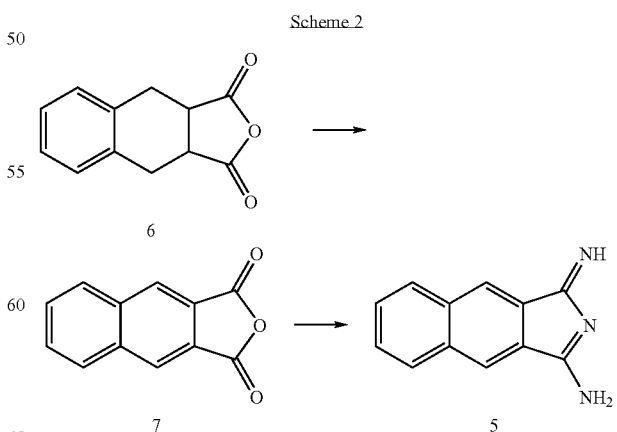

Tetrahydronaphthalic anhydride 6 was an attractive starting point, because this is a known Diels-Alder adduct which may be synthesized via the route shown in Scheme 3.

Scheme 3

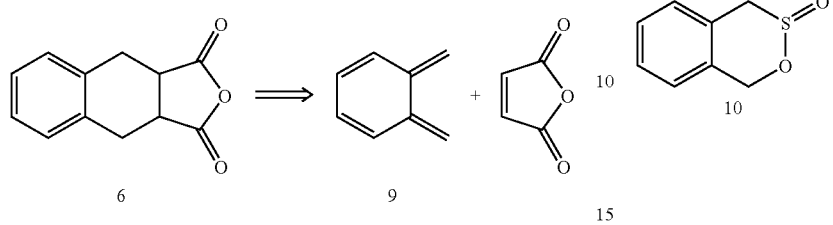

Referring to Scheme 2, it was hoped that the conversion of naphthalic anhydride 7 to the benzisoindolenine 5 would proceed analogously to the known conversion of phthalic anhydride to the isoindolenine 8, as described in WO98/31667.

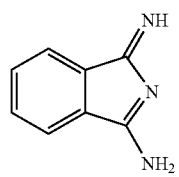

8

However, a number of problems remained with the route outlined in Scheme 2. Firstly, the dehydrogenation of tetrahydronaphthalic anhydride 6 typically requires high temperature catalysis. Under these conditions, tetrahydronaphthalic anhydride 6 readily sublimes resulting in very poor yields. Secondly, the preparation of tetrahydronaphthalic anhydride 6 on a large scale was not known. Whilst a number of small-scale routes to this compound were known in the literature, these generally suffered either from poor yields or scalability problems.

The use of sultines as diene precursors is well known and 1,4-dihydro-2,3-benzoxathiin-3-oxide 10 has been used in a synthesis of 6 on a small scale (Hoey, M. D.; Dittmer, D. A. *J. Org. Chem.* 1991, 56, 1947-1948). As shown in Scheme 4, this route commences with the relatively inexpensive dichloro-o-xylene 11, but the feasibility of scaling up this reaction sequence is limited by the formation of undesirable polymeric by-products in the sultine-forming step. The formation of these by-products makes reproducible production of 6 in high purity and high yield difficult.

Scheme 4

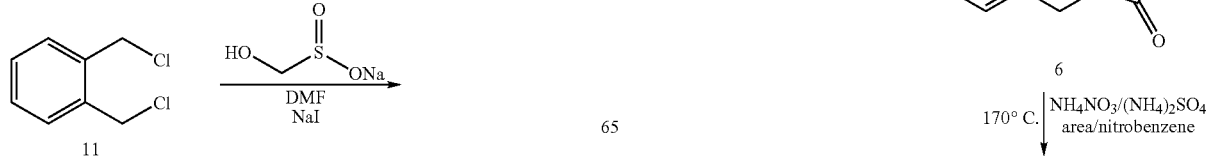

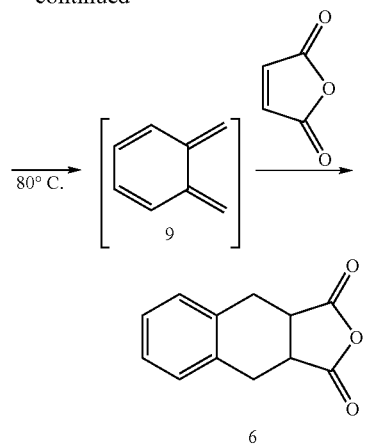

Nevertheless, the route outlined in Scheme 4 is potentially attractive from a cost standpoint, since dichloro-o-xylene 11 and maleic anhydride are both inexpensive materials.

Whilst the reaction sequence shown in Schemes 4 and 2 present significant synthetic challenges, the present inventors have surprisingly found that, using modified reaction conditions, the benzisoindolenine 5 can be generated on a large scale and in high yield. Hence, the present invention enables the production of naphthalocyanines from inexpensive starting materials, and represents a significant cost improvement over known syntheses, which start from napthalene-2,3-dicarbonitrile 2.

Referring to Scheme 5, there is shown a route to the benzisoindolenine 5, which incorporates two synthetic improvements in accordance with the present invention.

Scheme 5

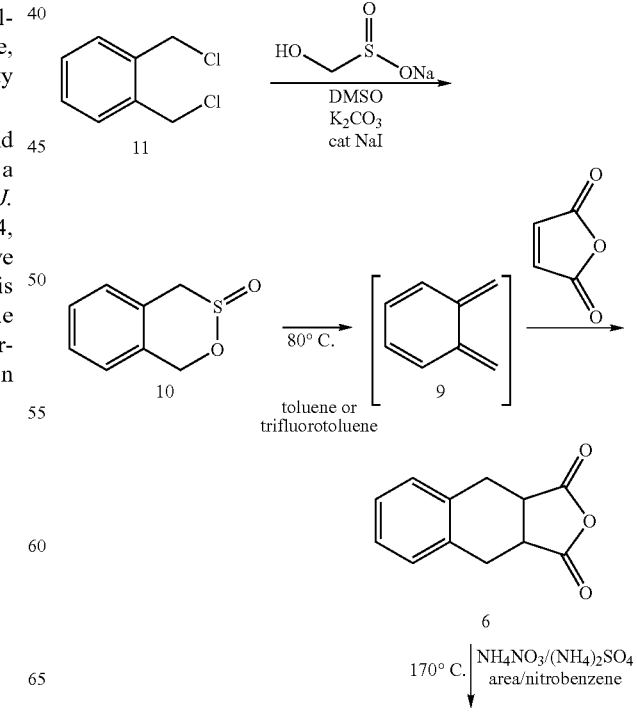

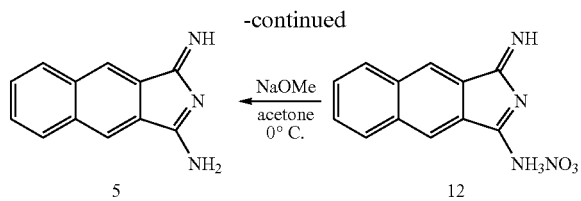

Unexpectedly, it was found that by using DMSO as the reaction solvent in the conversion of 11 into 10, the reaction rate and selectively for the formation of sultine 10 increases significantly. This is in contrast to known conditions (Hoey, M. D.; Dittmer, D. A. *J. Org. Chem.* 1991, 56, 1947-1948) employing DMF as the solvent, where the formation of undesirable polymeric side-products is a major problem, especially on a large scale. Accordingly, the present invention provides a significant improvement in the synthesis of tetrahydronaphthalic anhydride 6.

The present invention also provides a significant improvement in the conversion of tetrahydronaphthalic anhydride 6 to the benzisoindolenine 5. Surprisingly, it was found that the ammonium nitrate used for this step readily effects oxidation of the saturated ring system as well as converting the anhydride to the isoindolenine. Conversion to a tetrahydroisoindolenine was expected to proceed smoothly, in accordance with the isoindolenine similar systems described in WO98/31667. However, concomitant dehydrogenation under these reaction conditions advantageously provided a direct one-pot route from the tetrahydronaphthalic anhydride 6 to the benzisoindolenine salt 12. This avoids problematic and low-yielding dehydrogenation of the tetrahydronaphthalic anhydride 6 in a separate step. Subsequent treatment of the salt 12 with a suitable base, such as sodium methoxide, liberates the benzisoindolenine 5. As a result of these improvements, the entire reaction sequence from 11 to 5 is very conveniently carried out, and employs inexpensive starting materials and reagents (Scheme 5).

The benzisoindolenine 5 may be converted into any required naphthalocyanine using known conditions. For example, the preparation of gallium naphthalocyanine from benzisoindolenine 5 is exemplified herein. Subsequent manipulation of the naphthalocyanine macrocycle may also be performed in accordance with known protocols. For example, sulfonation may be performed using oleum, as described in U.S. Pat. Nos. 7,148,345 and 7,122,076.

Hitherto, the use of tetrahydronaphthalic anhydride 6 as a building block for naphthalocyanine synthesis had not previously been reported. However, it has now been shown that tetrahydronaphthalic anhydride 6 is a viable intermediate in the synthesis of these important compounds. Moreover, it is understood by the present inventors that the route shown in Scheme 5 represents the most cost-effective synthesis of benzisoindolenines 5.

The term "aryl" is used herein to refer to an aromatic group, such as phenyl, naphthyl or triptycenyl. $C_{6-12}$aryl, for example, refers to an aromatic group having from 6 to 12 carbon atoms, excluding any substituents. The term "arylene", of course, refers to divalent groups corresponding to the monovalent aryl groups described above. Any reference to aryl implicitly includes arylene, where appropriate.

The term "heteroaryl" refers to an aryl group, where 1, 2, 3 or 4 carbon atoms are replaced by a heteroatom selected from N, O or S. Examples of heteroaryl (or heteroaromatic) groups include pyridyl, benzimidazolyl, indazolyl, quinolinyl, isoquinolinyl, indolinyl, isoindolinyl, indolyl, isoindolyl, furanyl, thiophenyl, pyrrolyl, thiazolyl, imidazolyl, oxazolyl, isoxazolyl, pyrazolyl, isoxazolonyl, piperazinyl, pyrimidinyl, piperidinyl, morpholinyl, pyrrolidinyl, isothiazolyl, triazolyl, oxadiazolyl, thiadiazolyl, pyridyl, pyrimidinyl, benzopyrimidinyl, benzotriazole, quinoxalinyl, pyridazyl, coumarinyl etc. The term "heteroarylene", of course, refers to divalent groups corresponding to the monovalent heteroaryl groups described above. Any reference to heteroaryl implicitly includes heteroarylene, where appropriate.

Unless specifically stated otherwise, aryl and heteroaryl groups may be optionally substituted with 1, 2, 3, 4 or 5 of the substituents described below.

Where reference is made to optionally substituted groups (e.g. in connection with aryl groups or heteroaryl groups), the optional substituent(s) are independently selected from $C_{1-8}$alkyl, $C_{1-8}$alkoxy, $—(OCH_2CH_2)_3OR^d$ (wherein d is an integer from 2 to 5000 and $R^d$ is H, $C_{1-8}$alkyl or $C(O)C_{1-8}$alkyl), cyano, halogen, amino, hydroxyl, thiol, $—SR^v$, $—NR^uR^v$, nitro, phenyl, phenoxy, $—CO_2R^v$, $—C(O)R^v$, $—OCOR^v$, $—SO_2R^v$, $—OSO_2R^v$, $—SO_2OR^v$, $—NHC(O)R^v$, $—CONR^uR^v$, $—CONR^uR^v$, $—SO_2NR^uR^v$, wherein $R^u$ and $R^v$ are independently selected from hydrogen, $C_{1-20}$alkyl, phenyl or phenyl-$C_{1-8}$alkyl (e.g. benzyl). Where, for example, a group contains more than one substituent, different substituents can have different $R^u$ or $R^v$ groups.

The term "alkyl" is used herein to refer to alkyl groups in both straight and branched forms. Unless stated otherwise, the alkyl group may be interrupted with 1, 2, 3 or 4 heteroatoms selected from O, NH or S. Unless stated otherwise, the alkyl group may also be interrupted with 1, 2 or 3 double and/or triple bonds. However, the term "alkyl" usually refers to alkyl groups having double or triple bond interruptions. Where "alkenyl" groups are specifically mentioned, this is not intended to be construed as a limitation on the definition of "alkyl" above.

Where reference is made to, for example, $C_{1-20}$alkyl, it is meant the alkyl group may contain any number of carbon atoms between 1 and 20. Unless specifically stated otherwise, any reference to "alkyl" means $C_{1-20}$alkyl, preferably $C_{1-12}$alkyl or $C_{1-6}$alkyl.

The term "alkyl" also includes cycloalkyl groups. As used herein, the term "cycloalkyl" includes cycloalkyl, polycycloalkyl, and cycloalkenyl groups, as well as combinations of these with linear alkyl groups, such as cycloalkylalkyl groups. The cycloalkyl group may be interrupted with 1, 2 or 3 heteroatoms selected from O, N or S. However, the term "cycloalkyl" usually refers to cycloalkyl groups having no heteroatom interruptions. Examples of cycloalkyl groups include cyclopentyl, cyclohexyl, cyclohexenyl, cyclohexylmethyl and adamantyl groups.

The term "arylalkyl" refers to groups such as benzyl, phenylethyl and naphthylmethyl.

The term "halogen" or "halo" is used herein to refer to any of fluorine, chlorine, bromine and iodine. Usually, however, halogen refers to chlorine or fluorine substituents.

Where reference is made herein to "a naphthalocyanine", "a benzisoindolenine", "a tetrahydronaphthalic anhydride" etc, this is understood to be a reference to the general class of compounds embodied by these generic names, and is not intended to refer to any one specific compound. References to specific compounds are accompanied with a reference numeral.

Chiral compounds described herein have not been given stereo-descriptors. However, when compounds may exist in stereoisomeric forms, then all possible stereoisomers and mixtures thereof are included (e.g. enantiomers, diastereomers and all combinations including racemic mixtures etc.).

Likewise, when compounds may exist in a number of regioisomeric or tautomeric forms, then all possible regioisomers, tautomers and mixtures thereof are included.

For the avoidance of doubt, the term "a" (or "an"), in phrases such as "comprising a", means "at least one" and not "one and only one". Where the term "at least one" is specifically used, this should not be construed as having a limitation on the definition of "a".

Throughout the specification, the term "comprising", or variations such as "comprise" or "comprises", should be construed as including a stated element, integer or step, but not excluding any other element, integer or step.

The invention will now be described with reference to the following drawings and examples. However, it will of course be appreciated that this invention may be embodied in many other forms without departing from the scope of the invention, as defined in the accompanying claims.

Example 1

1,4-dihydro-2,3-benzoxathiin-3-oxide 10

Sodium hydroxymethanesulfinate (Rongalite™) (180 g; 1.17 mol) was suspended in DMSO (400 mL) and left to stir for 10 min. before dichloro-o-xylene (102.5 g; 0.59 mol), potassium carbonate (121.4 g; 0.88 mol) and sodium iodide (1.1 g; 7 mmol) were added consecutively. More DMSO (112 mL) was used to rinse residual materials into the reaction mixture before the whole was allowed to stir at room temperature. The initial endothermic reaction became mildly exothermic after around 1 h causing the internal temperature to rise to ca. 32-33° C. The reaction was followed by TLC (ethyl acetate/hexane, 50:50) and found to be complete after 3 h. The reaction mixture was diluted with methanol/ethyl acetate (20:80; 400 mL) and the solids were filtered off, and washed with more methanol/ethyl acetate (20:80; 100 mL, 2×50 mL). The filtrate was transferred to a separating funnel and brine (1 L) was added. This caused more sodium chloride from the product mixture to precipitate out. The addition of water (200 mL) redissolved the sodium chloride. The mixture was shaken and the organic layer was separated and then the aqueous layer was extracted further with methanol/ethyl acetate (20:80; 200 mL, 150 mL, 250 mL). The combined extracts were dried ($Na_2SO_4$) and rotary evaporated (bath 37-38° C.). More solvent was removed under high vacuum to give the sultine 10 as a pale orange liquid (126 g) that was found by $^1H$ NMR spectroscopy to be relatively free of by-product but containing residual DMSO and ethyl acetate (FIG. 1).

Example 2

Tetrahydronaphthalic anhydride 6

The crude sultine from above (126 g) was diluted in trifluorotoluene (100 mL) and then added to a preheated (bath 80° C.) suspension of maleic anhydride (86 g; 0.88 mol) in trifluorotoluene (450 mL). The residual sultine was washed with more trifluorotoluene into the reaction mixture and then the final volume was made up to 970 mL. The reaction mixture was heated at 80° C. for 15 h, more maleic anhydride (28.7 g; 0.29 mol) was added and then heating was continued for a further 8 h until TLC showed that the sultine had been consumed. While still at 80° C., the solvent was removed by evaporation with a water aspirator and then the residual solvent was removed under high vacuum. The moist solid was triturated with methanol (200 mL) and filtered off, washing with more methanol (3×100 mL). The tetrahydronaphthalic anhydride 6 was obtained as a fine white crystalline solid (75.4 g; 64% from 10) after drying under high vacuum at 60-70° C. for 4 h.

Example 3

The sultine was prepared from dichloro-o-xylene (31.9 g; 0.182 mol), as described in Example 2, and then reacted with maleic anhydride (26.8 g; 0.273 mol) in toluene (300 mL total volume) as described above. This afforded the tetrahydronaphthale anhydride 6 as a white crystalline solid (23.5 g; 64%).

Example 4

1-amino-3-iminobenz[f]isoindolenine Nitrate Salt 12

Urea (467 g; 7.78 mol) was added to a mechanically stirred mixture of ammonium sulfate (38.6 g; 0.29 mol), ammonium molybdate (1.8 g) and nitrobenzene (75 mL). The whole was heated with a heating mantle to ca. 130° C. (internal temperature) for 1 h causing the urea to melt. At this point the anhydride 6 (98.4 g; 0.49 mol) was added all at once as a solid. After 15 min ammonium nitrate (126.4 g; 1.58 mol) was added with stirring (internal temperature 140° C.) accompanied by substantial gas evolution. The reaction temperature was increased to 170-175° C. over 45 min and held there for 2 h 20 min. The viscous brown mixture was allowed to cool to ca. 100° C. and then methanol (400 mL) was slowly introduced while stirring. The resulting suspension was poured on a sintered glass funnel, using more methanol (100 mL) to rinse out the reaction flask. After removing most of the methanol by gravity filtration, the brown solid was sucked dry and then washed with more methanol (3×200 mL, 50 mL), air-dried overnight and dried under high vacuum in a warm water bath for 1.5 h. The benzisoindolenine salt 12 was obtained as a fine brown powder (154.6 g) and was found by NMR analysis to contain urea (5.43 ppm) and other salts (6.80 ppm). This material was used directly in the next step without further purification.

Example 5

1-amino-3-iminobenz[f]isoindolenine 7

The crude nitrate salt 12 (154.6 g) was supported in acetone (400 mL) with cooling in an ice/water bath to 0° C. Sodium methoxide (25% in methanol; 284 ml; 1.3 mol) was slowly dropwise via a dropping funnel at such a rate as to maintain an internal temperature of 0-5° C. Upon completion of the addition, the reaction mixture was poured into cold water (2×2 L) in two 2 L conical flasks. The mixtures were then filtered on sintered glass funnels and the solids were washed thoroughly with water (250 mL; 200 mL for each funnel). The fine brown solids were air-dried over 2 days and then further dried under high vacuum to give the benzisoindolenine 5 as a fine brown powder (69.1 g; 73%).

Example 6

Naphthalocyanatogallium methoxytriethyleneoxide

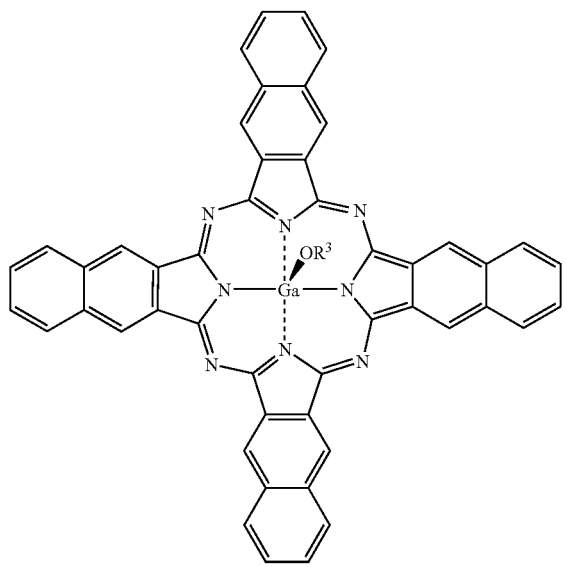

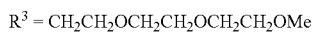

R³ = CH₂CH₂OCH₂CH₂OCH₂CH₂OMe

Figure 7:
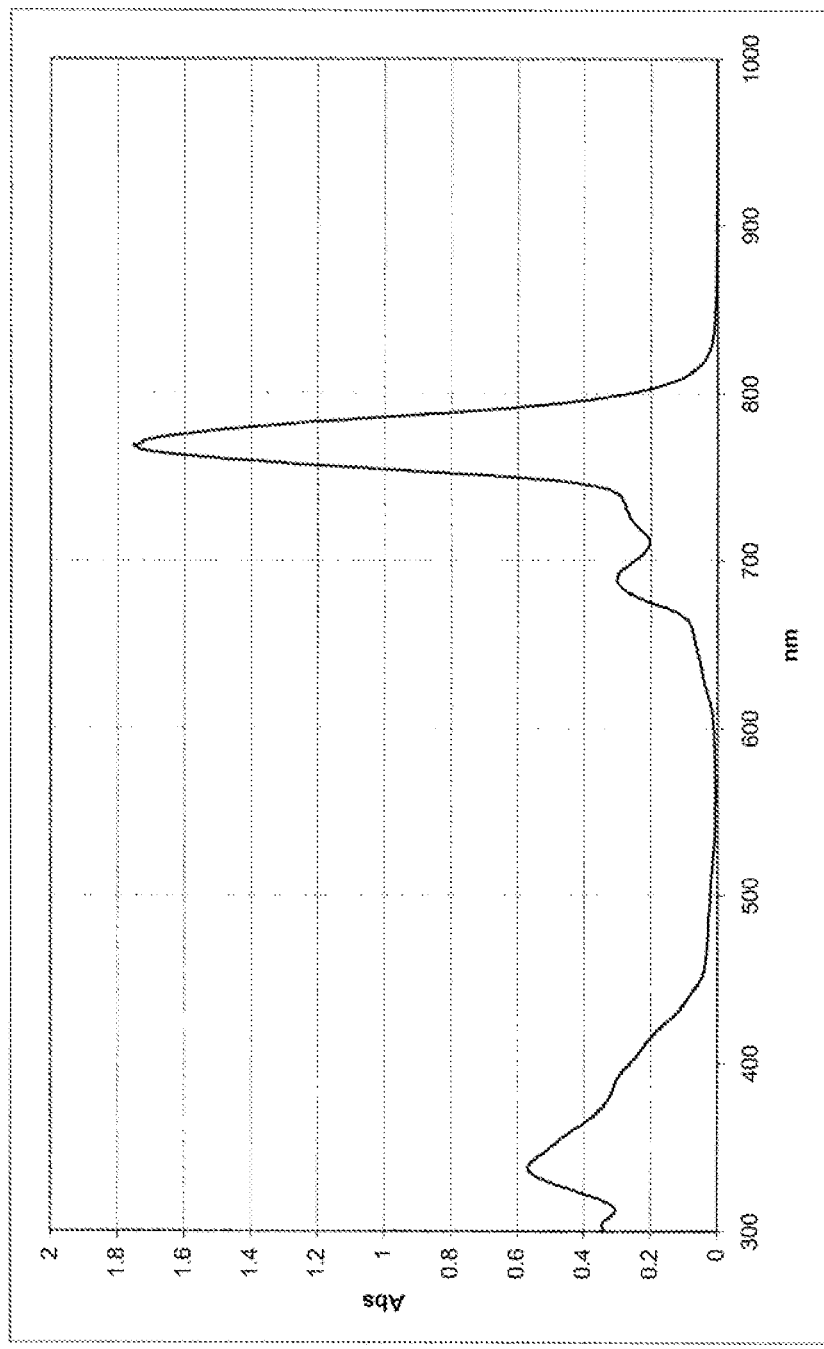
FIG. 7 is a UV-VIS spectrum of naphthalocyanatogallium methoxytriethyleneoxide in NMP.

Gallium chloride (15.7 g; 0.89 mol) was dissolved in anhydrous toluene (230 mL) in a 3-neck flask (1 L) equipped with a mechanical stirrer, heating mantle, thermometer, and distillation outlet. The resulting solution was cooled in an ice/water bath to 10° C. and then sodium methoxide in methanol (25%; 63 mL) was added slowly with stirring such that the internal temperature was maintained below 25° C. thereby affording a white precipitate. The mixture was then treated with triethylene glycol monomethyl ether (TEGMME: 190 mL) and then the whole was heated to distill off all the methanol and toluene (3 h). The mixture was then cooled to 90-100° C. (internal temperature) by removing the heating mantle and then the benzisoindolenine 5 from the previous step (69.0 g; 0.35 mol) was added all at once as a solid with the last traces being washed into the reaction vessel with diethyl ether (30 mL). The reaction mixture was then placed in the preheated heating mantle such that an internal temperature of 170° C. was established after 20 min. Stirring was then continued at 175-180° C. for a further 3 h during which time a dark green/brown colour appeared and the evolution of ammonia took place. The reaction mixture was allowed to cool to ca. 100° C. before diluting with DMF (100 mL) and filtering through a sintered glass funnel under gravity overnight. The moist filter cake was sucked dry and washed consecutively with DMF (80 mL), acetone (2×100 mL), water (2×100 mL), DMF (50 mL), acetone (2×50 mL; 100 mL) and diethyl ether (100 mL) with suction. After brief air drying, the product was dried under high vacuum at 60-70° C. to constant weight. Naphthalocyanatogallium methoxytriethyleneoxide was obtained as a microcrystalline dark blue/green solid (60.7 g; 76%); $\lambda_{max}$ (NMP) 771 nm (FIG. 7).

The invention claimed is:

1. A method of effecting a one-pot conversion of a tetrahydronaphthalic anhydride of formula (I):

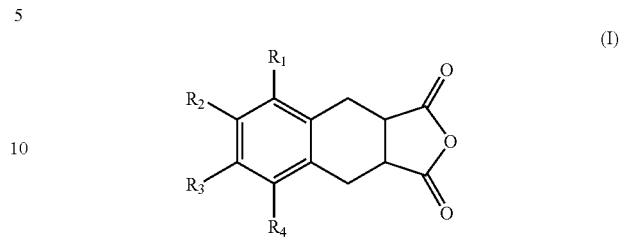

to a salt of a benzisoindolenine of formula (II):

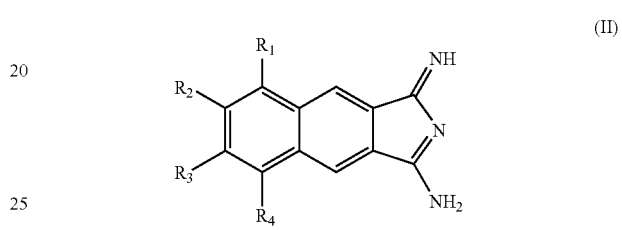

said method comprising heating said tetrahydronaphthalic anhydride of formula (I) with a reagent mixture comprising ammonium nitrate, wherein:

$R_1$, $R_2$, $R_3$ and $R_4$ are each independently selected from hydrogen, hydroxyl, $C_{1-20}$ alkyl, $C_{1-20}$ alkoxy, amino, $C_{1-20}$ alkylamino, di($C_{1-20}$ alkyl)amino, halogen, cyano, thiol, $C_{1-20}$ alkylthio, nitro, $C_{1-20}$ alkylcarboxy, $C_{1-20}$ alkylcarbonyl, $C_{1-20}$ alkoxycarbonyl, $C_{1-20}$ alkylcarbonyloxy, $C_{1-20}$ alkylcarbonylamino, $C_{5-20}$ aryl, $C_{5-20}$ arylalkyl, $C_{5-20}$ aryloxy, $C_{5-20}$ arylalkoxy, $C_{5-20}$ heteroaryl, $C_{5-20}$ heteroaryloxy, $C_{5-20}$ heteroarylalkoxy or $C_{5-20}$ heteroarylalkyl.

2. The method of claim 1, wherein $R_1$, $R_2$, $R_3$ and $R_4$ are all hydrogen.

3. The method of claim 1, wherein said salt of said benzisoindolenine of formula (II) is a nitrate salt.

4. The method of claim 1, wherein said reagent mixture comprises at least 2 equivalents of ammonium nitrate with respect to said tetrahydronaphthalic anhydride.

5. The method of claim 1, wherein said reagent mixture comprises urea.

6. The method of claim 1, wherein said reagent mixture comprises at least one further ammonium salt.

7. The method of claim 5, wherein said at least one further ammonium salt is selected from ammonium sulfate and ammonium benzenesulfonate.

8. The method of claim 1, wherein said reagent mixture comprises a catalytic amount of ammonium molybdate.

9. The method of claim 1, wherein said heating is within a temperature range of 150 to 200° C.

10. The method of claim 8, wherein said heating is in the presence of solvent selected from the group comprising: nitrobenzene, diphenyl, diphenyl ether, mesitylene, anisole, phenetole, dichlorobenzene, trichlorobenzene and mixtures thereof.

11. The method of claim 1, comprising the further step of liberating the corresponding benzisoindolenine from the salt of the benzisoindolenine of formula (II) using a base.

* * * * *